US009220530B2

(12) United States Patent
Moberg

(10) Patent No.: US 9,220,530 B2
(45) Date of Patent: Dec. 29, 2015

(54) EASILY CLEANED ATHERECTOMY CATHETERS AND METHODS OF USE

(71) Applicant: Covidien LP, Mansfield, MA (US)

(72) Inventor: John Robert Moberg, Elk River, MN (US)

(73) Assignee: Covidien LP, Mansfield, MA (US)

( * ) Notice: Subject to any disclaimer, the term of this patent is extended or adjusted under 35 U.S.C. 154(b) by 195 days.

(21) Appl. No.: 14/039,736

(22) Filed: Sep. 27, 2013

(65) Prior Publication Data

US 2014/0088625 A1   Mar. 27, 2014

Related U.S. Application Data

(60) Continuation of application No. 13/460,875, filed on May 1, 2012, now Pat. No. 8,574,249, which is a division of application No. 12/780,107, filed on May 14, 2010, now Pat. No. 8,192,452.

(60) Provisional application No. 61/178,119, filed on May 14, 2009.

(51) Int. Cl.
*A61B 17/22* (2006.01)
*A61B 17/3207* (2006.01)

(52) U.S. Cl.
CPC . *A61B 17/320758* (2013.01); *A61B 17/320783* (2013.01); *A61B 2017/320716* (2013.01); *A61B 2017/320775* (2013.01); *A61B 2017/320791* (2013.01)

(58) Field of Classification Search
USPC ............................................ 606/159; 604/22
See application file for complete search history.

(56) References Cited

U.S. PATENT DOCUMENTS

| 1,481,078 | A | 1/1924  | Albertson |
| 2,178,790 | A | 11/1939 | Henry     |
| 2,701,559 | A | 2/1955  | Cooper    |
| 2,850,007 | A | 9/1958  | Lingley   |
| 3,064,651 | A | 11/1960 | Henderson |
| 3,082,805 | A | 3/1963  | Royce     |
| 3,320,957 | A | 5/1967  | Sokolik   |

(Continued)

FOREIGN PATENT DOCUMENTS

| CA | 2000621    | 4/1990  |
| DE | 3732236 C1 | 12/1988 |

(Continued)

OTHER PUBLICATIONS

Notice of Preliminary Rejection for Korean Application No. 10-2013-7013071 with English translation, May 14, 2015, 4 pages.

(Continued)

*Primary Examiner* — Tuan V Nguyen

(57) ABSTRACT

An atherectomy catheter is provided having a tissue collection chamber capable of being cleaned out in a simple, fast and effective way, and also provides methods of using said catheter to remove material from a blood vessel lumen. In one embodiment the tissue collection chamber has an expandable tip having a first closed position capable of retaining material in the chamber and having a second open position that may allow expulsion of material from the chamber. In a second embodiment the tissue collection chamber has a displaceable tip having a first closed position to retain material in the chamber and having a second open position to allow expulsion of material from the chamber.

20 Claims, 10 Drawing Sheets

(56) References Cited

U.S. PATENT DOCUMENTS

| | | |
|---|---|---|
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundy et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |

(56) References Cited

U.S. PATENT DOCUMENTS

| | | |
|---|---|---|
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |

(56) References Cited

U.S. PATENT DOCUMENTS

| | | |
|---|---|---|
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |

(56) References Cited

U.S. PATENT DOCUMENTS

| | | |
|---|---|---|
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,192,452 B2 * | 6/2012 | Moberg .................. 606/159 |
| 8,574,249 B2 * | 11/2013 | Moberg .................. 606/159 |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson et al. |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |

(56) References Cited

U.S. PATENT DOCUMENTS

| | | |
|---|---|---|
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |

OTHER PUBLICATIONS

Chinese Notification of First Office Action for CN Application No. 201080027813.X dated Oct. 10, 2013, 11 pages, Beijing, China. (with English translation).

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

KIPO's Notice of Preliminary Rejection for Korean Application No. 10-2011-7029796, dated Mar. 28, 2013, 5 pages, Korea. (with English translation).

Russian Office Action for RU Application No. 2011146087/14(068993), dated Jun. 11, 2013, 7 pages, Moscow, Russia. (with English translation).

USPTO Non-Final Office action for U.S. Appl. No. 13/460,875, dated Jan. 7, 2013, 9 pages.

Amendment A for U.S. Appl. No. 13/460,875, dated Apr. 8, 2013, 13 pages.

USPTO Final Office action for U.S. Appl. No. 13/460,875, dated May 14, 2013, 9 pages, Alexandria, Virginia, United States.

Amendment B for U.S. Appl. No. 13/460,875, dated Mar. 13, 2013, 7 pages.

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Patent Examination Report No. 1 for AU Application No. 2010248909 dated Jul. 25, 2012, 2 pages, Australia.

Canadian Examination Report for CA Application No. 2,761,774 dated May 30, 2013, 2 pages, Toronto, Ontario, Canada.

* cited by examiner

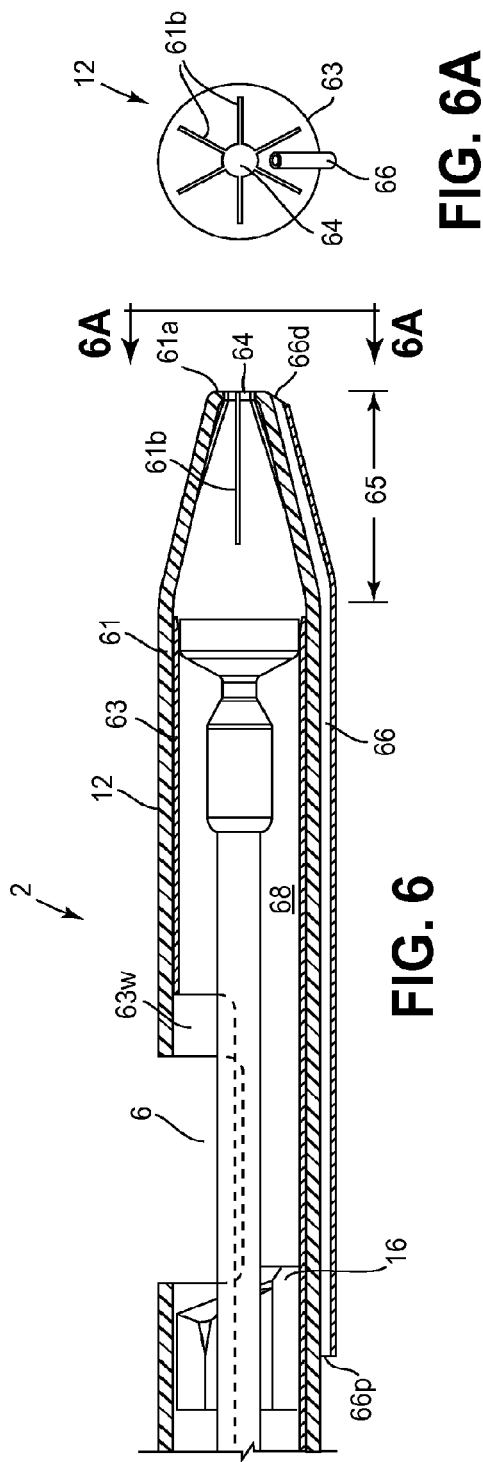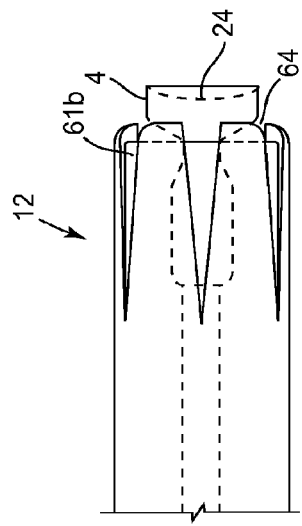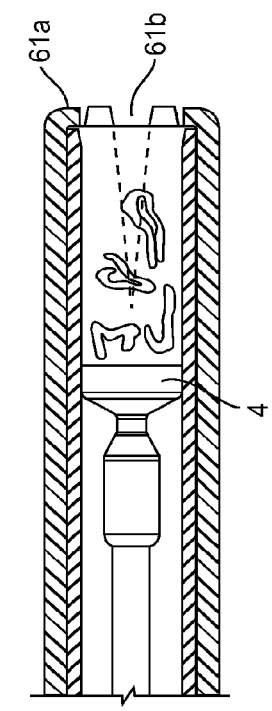

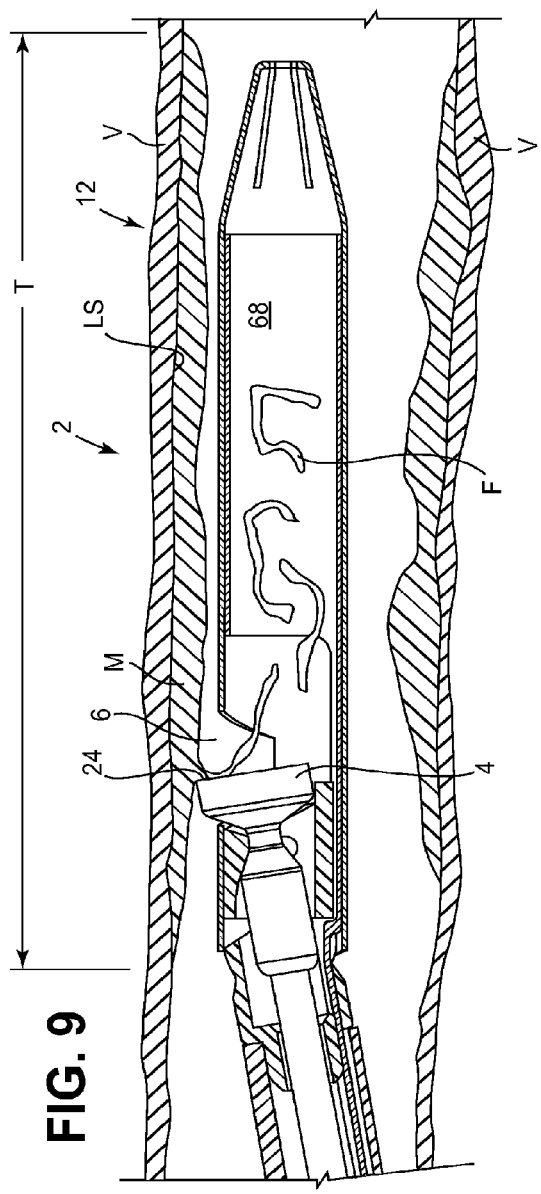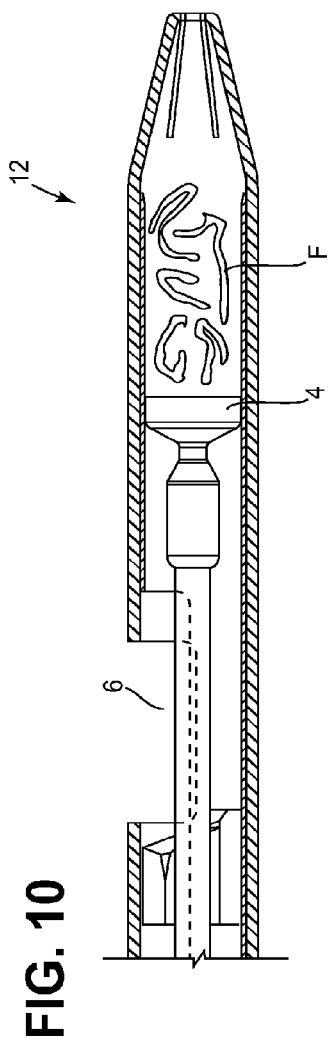

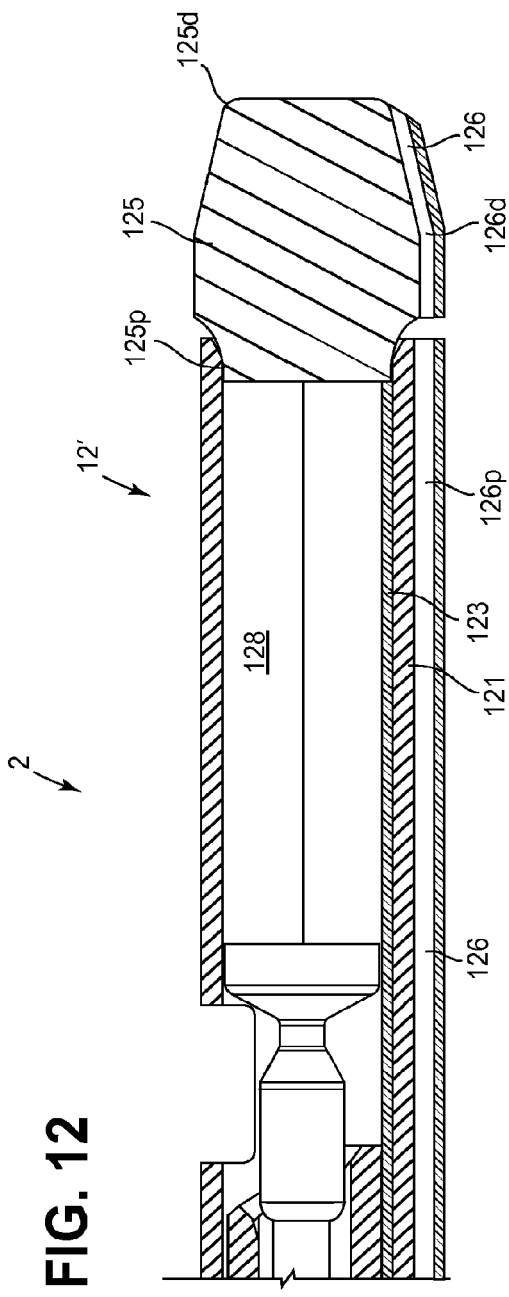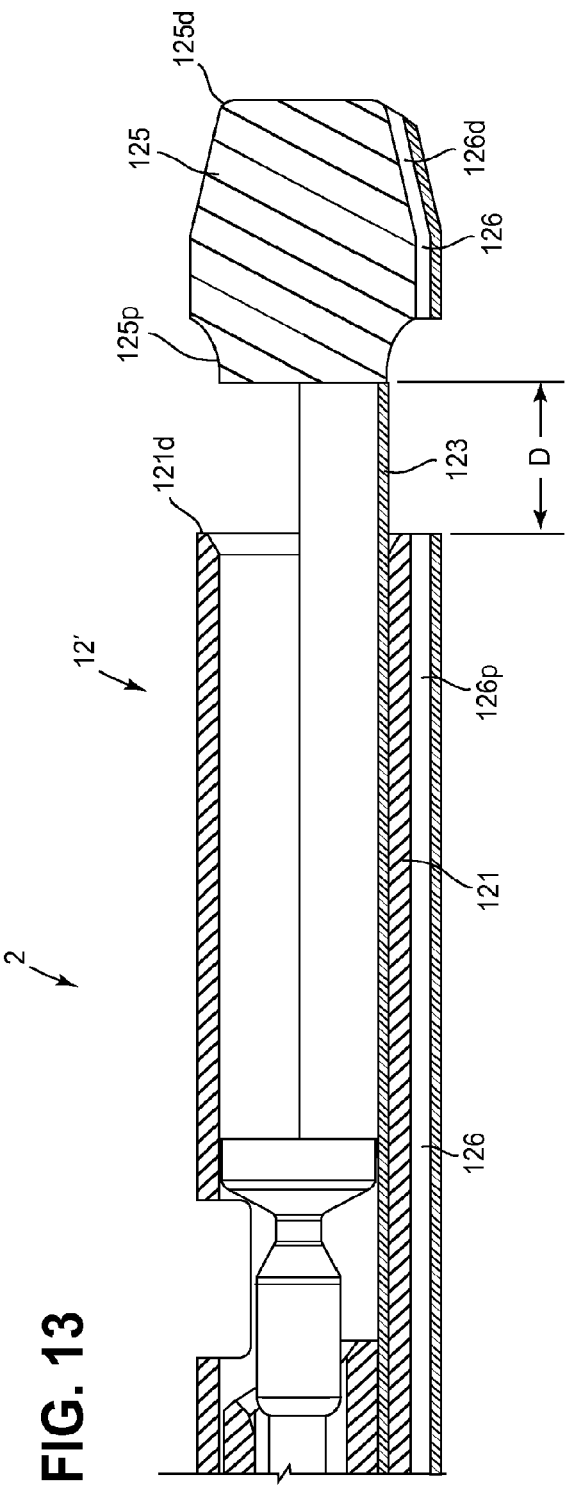

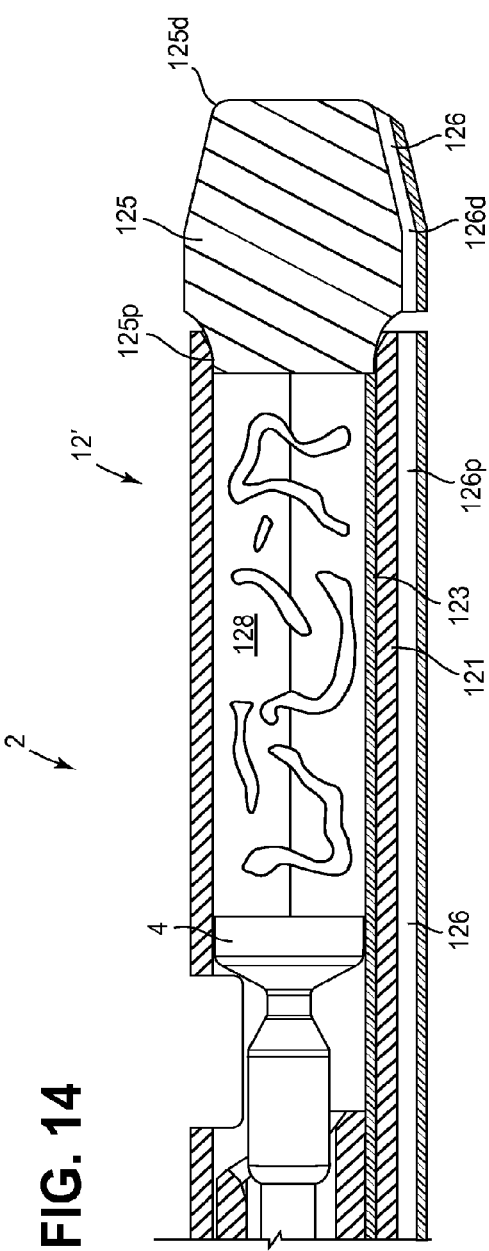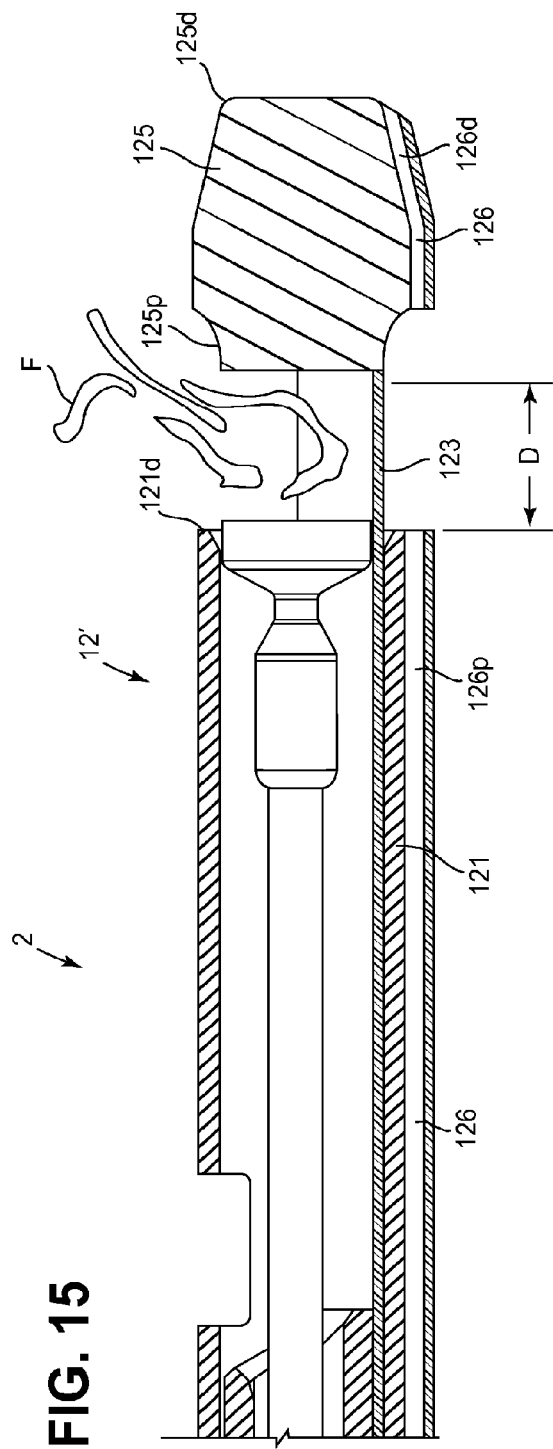

EASILY CLEANED ATHERECTOMY CATHETERS AND METHODS OF USE

This application is a continuation application of U.S. application Ser. No. 13/460,875, filed May 1 ,2012, now U.S. Pat. No. 8,574,249, which is a divisional of U.S. application Ser. No. 12/780,107, filed May 14, 2010, now U.S. Pat. No. 8,192, 452, which clams the benefit of U.S. Provisional Patent Application No. 61/178,119, filed May 14, 2009, the contents of each of which are hereby incorporated by reference herein.

FIELD OF THE INVENTION

The present invention relates to catheters used to remove material from a site in a body lumen. More particularly, this invention pertains to removal of material stored in such a catheter.

BACKGROUND OF THE INVENTION

Atherosclerosis is a progressive disease of the vascular system whereby atheroma is deposited on the inner walls of blood vessels. Over time atheromatous deposits can become large enough to reduce or occlude blood flow through the vessels, leading to symptoms of low blood flow such as pain in the legs (on walking or at rest), skin ulcer, angina (at rest or exertional), and other symptoms. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods. However these methods undesirably tear and stretch the vessel, causing scar formation in a high percentage of patients. Such scar tissue (restenotic material), once formed, blocks flow in the vessel and often needs to be removed. The deposits can be pulverized using lasers and other methods. However pulverization alone of atheromatous material allows microemboli to flow downstream and lodge in distal vascular beds, further compromising blood flow to the tissue affected by the disease. Atherectomy catheters can be used to remove atheromatous deposits from the blood vessel and can present an ideal solution when the deposits removed from the vessel are captured and removed from the body. One way to capture and remove such deposits is to store the deposits within the catheter and to subsequently remove the catheter from the body.

One problem that occurs when storing material or deposits in a catheter is that the catheter can have insufficient storage capacity. The portion of the vessel to be treated can be quite extensive. For example, the portion of the vessel to be treated can extend over a vessel length of 200 mm or longer. If the storage chamber in the catheter becomes filled with material the catheter must be removed from the body, the deposits removed from the catheter, and the catheter re-inserted into the body for more deposit removal and storage. However, present methods for removing deposits from catheter collection chambers can be time consuming.

What is needed is a catheter having a simple, fast and effective way of removing deposits from a catheter collection chamber.

SUMMARY OF THE INVENTION

The present invention provides an atherectomy catheter having a tissue collection chamber capable of being cleaned out in a simple, fast and effective way, and also provides methods of using the catheter to remove material from a blood vessel lumen. In one embodiment the tissue collection chamber has an expandable tip having a first closed position capable of retaining material in the chamber and having a second open position that may allow expulsion of material from the chamber. In a second embodiment the tissue collection chamber has a displaceable tip having a first closed position to retain material in the chamber and having a second open position to allow expulsion of material from the chamber.

The invention provides an atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction. The tissue collection chamber has a first closed position capable of retaining cut tissue in the chamber and a second open position capable of allowing expulsion of cut tissue from the chamber. The tissue collection chamber comprises an expandable tip at a distal region of the catheter, the expandable tip having a first closed position capable of retaining cut tissue in the chamber and a second open position capable of allowing expulsion of cut tissue from a distal opening at a distal end of the chamber.

The invention provides an atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction. The tissue collection chamber has a first closed position capable of retaining cut tissue in the chamber and a second open position capable of allowing expulsion of cut tissue from the chamber. The tissue collection chamber comprises a displaceable tip at a distal region of the catheter, the displaceable tip having a first closed position capable of retaining cut tissue in the chamber and a second open position capable of allowing expulsion of cut tissue from the chamber, the displaceable tip being attached to the atherectomy catheter in both the first closed and second open positions.

The invention provides a method of removing material from a body lumen, the method comprising: providing an atherectomy catheter, the atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction, wherein the tissue collection chamber has a first closed position capable of retaining cut tissue in the chamber and a second open position capable of allowing expulsion of cut tissue from the chamber, and wherein the tissue collection chamber comprises an expandable tip at a distal region of the catheter, the expandable tip having a first closed position capable of retaining cut tissue in the chamber and a second open position capable of allowing expulsion of cut tissue from a distal opening at a distal end of the chamber; placing the catheter in the body lumen; and moving the catheter in the body lumen to contact the cutting element with the material in the body lumen.

The invention provides a method of removing material from a body lumen, the method comprising: providing an atherectomy catheter, the atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction, wherein the tissue collection chamber has a first closed position capable of retaining cut tissue in the chamber and a second open position capable of allowing expulsion of cut tissue from the chamber, and wherein the tissue collection chamber comprises a displaceable tip at a distal region of the catheter, the displaceable tip having a first closed position capable of retaining cut tissue in the chamber and a second open position capable of allowing expulsion of cut tissue from the chamber, the displaceable tip being attached to the atherectomy catheter in both the first closed and second open positions; placing the catheter in the body lumen; and moving the catheter in the body lumen to contact the cutting element with the material in the body lumen.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 6 and 7 illustrate partial cross section views of a portion of an atherectomy catheter.

FIG. 6A illustrates an end view of the atherectomy catheter illustrated in FIG. 6.

FIG. 8 illustrates a side view of a portion of the catheter illustrated in FIGS. 6, 6A and 7.

FIGS. 9, 10 and 11 illustrate partial cross section views of a portion of the atherectomy catheter illustrated in FIGS. 6, 6A, 7 and 8 in various stages of use.

FIGS. 12 and 13 illustrate partial cross section views of a portion of another atherectomy catheter.

FIGS. 14 and 15 illustrate partial cross section views of a portion of the atherectomy catheter illustrated in FIGS. 12 and 13 in various stages of use.

DETAILED DESCRIPTION

Figure 1:
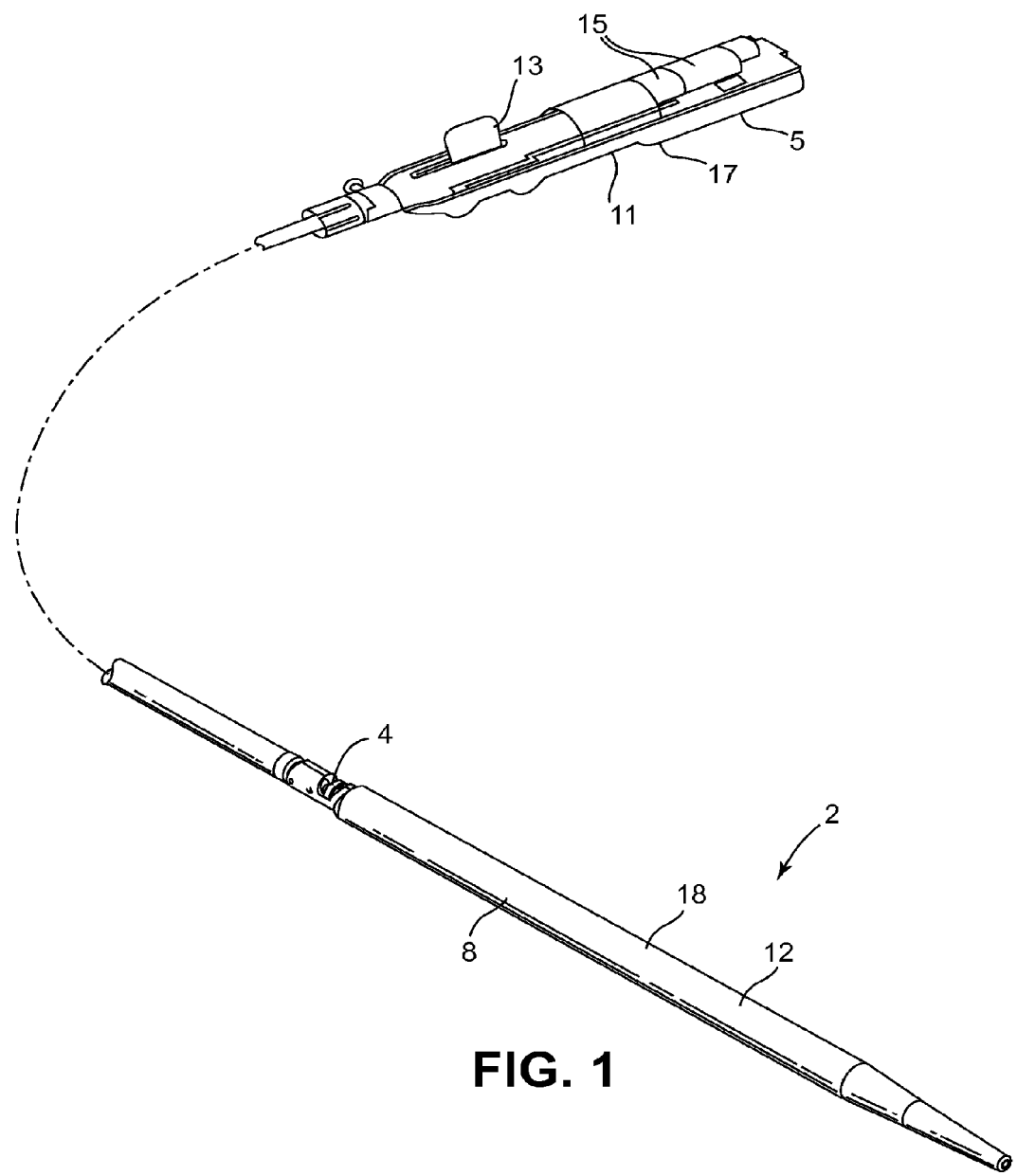
FIG. 1 illustrates an isometric view of an atherectomy catheter.

The invention provides an atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction. The tissue collection chamber has a first closed position capable of retaining cut tissue in the chamber and a second open position capable of allowing expulsion of cut tissue from the chamber. The tissue collection chamber comprises an expandable tip at a distal region of the catheter, the expandable tip having a first closed position capable of retaining cut tissue in the chamber and a second open position capable of allowing expulsion of cut tissue from a distal opening at a distal end of the chamber. In an embodiment, the tissue collection chamber comprises a sheath having a lumen.

In one embodiment, the tissue collection chamber comprises one or more slots in a distal region of the sheath. In another embodiment, the tissue collection chamber comprises two or more slots in a distal region of the sheath. The distal region of the sheath may comprise 2, 3, 4, 6, 8, 12, or 16 slots. In an embodiment, the distal region of the sheath has a distally tapering diameter. In one embodiment, the tissue collection chamber has a distal opening in the first closed position.

In an embodiment, the tissue collection chamber comprises a shim sleeve disposed within the lumen of the sheath, the shim sleeve being axially slidable relative to the sheath, and the shim sleeve having a lumen. In one embodiment, the shim sleeve may comprise a window. In an embodiment, the cutting element may be deployed through the shim sleeve window and the opening of the catheter. In an embodiment, the distal region of the sheath can be expanded by moving the shim sleeve distally. In one embodiment, the sheath is preprogrammed to assume the first closed position.

In one embodiment, the cutting element can be extended distally through the lumen of the shim sleeve. In an embodiment, the cutting element can be extended distally through a distal opening of the sheath when the tissue collection chamber is in the second open position. In one embodiment, the tissue collection chamber comprises a guidewire lumen.

In one embodiment, the tissue collection chamber comprises one or more slots in a distal region of the sheath, the distal region of the sheath has a distally tapering diameter, and the tissue collection chamber comprises a shim sleeve disposed within the sheath, the shim sleeve being axially slidable relative to the sheath, and the shim sleeve having a lumen. In an embodiment, the distal region of the sheath can be expanded by moving the shim sleeve distally.

The invention provides an atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction. The tissue collection chamber has a first closed position capable of retaining cut tissue in the chamber and a second open position capable of allowing expulsion of cut tissue from the chamber. The tissue collection chamber comprises a displaceable tip at a distal region of the catheter, the displaceable tip having a first closed position capable of retaining cut tissue in the chamber and a second open position capable of allowing expulsion of cut tissue from the chamber, the displaceable tip being attached to the atherectomy catheter in both the first closed and second open positions. In one embodiment, the tissue collection chamber comprises a sheath having a lumen. In an embodiment, the displaceable tip is axially slidable relative to the sheath. In an embodiment, the displaceable tip is disposed on a push shaft that is axially slidable relative to the sheath. In one embodiment, the push shaft is received within the lumen of the sheath. In an embodiment, the push shaft has a partially circular cross section. In another embodiment, the push shaft has an approximately semi-circular cross section.

In an embodiment, a proximal portion of the displaceable tip has a reduced diameter and is capable of being received within the lumen of the sheath. In one embodiment, a distal region of the displaceable tip has a distally tapering diameter.

In one embodiment, the cutting edge is a radially outer edge of the cutting element. In an embodiment, the cutting element is movable between a stored position and a cutting position relative to the opening. In one embodiment, the cutting element is moved between the stored position and the cutting position by sliding the cutting element against a cam surface. In one embodiment, a distal portion of the catheter relative to a proximal portion is deflected by sliding the cutting element against the cam surface.

The invention provides a method of removing material from a body lumen, the method comprising: providing an atherectomy catheter, the atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction, wherein the tissue collection chamber has a first closed position capable of retaining cut tissue in the chamber and a second open position capable of allowing expulsion of cut tissue from the chamber, and wherein the tissue collection chamber comprises an expandable tip at a distal region of the catheter, the expandable tip having a first closed position capable of retaining cut tissue in the chamber and a second open position capable of allowing expulsion of cut tissue from a distal opening at a distal end of the chamber; placing the catheter in the body lumen; and moving the catheter in the body lumen to contact the cutting element with the material in the body lumen. In one embodiment, the catheter is moved in a distal direction to contact the cutting edge with the material in the body lumen. In an embodiment, the catheter is placed in the body lumen with the cutting element in a stored position and the catheter is moved to contact the material with the cutting element in a cutting position.

In one embodiment, the method further comprises collecting the material in the tissue collection chamber, removing the catheter from the body lumen, and removing the material from the tissue collection chamber after the catheter has been removed from the body lumen. In an embodiment, the catheter is removed from the body lumen with the tissue collection chamber in the first closed position and the material is removed from the tissue collection chamber with the tissue collection chamber in a second open position capable of allowing expulsion of cut tissue from the chamber.

The invention provides a method of removing material from a body lumen, the method comprising: providing an atherectomy catheter, the atherectomy catheter comprising: a body having an opening; a rotatable shaft coupled to the body, the rotatable shaft being rotatable about a longitudinal axis of the shaft; a tissue collection chamber coupled to the body and positioned distal to the cutting element; and a cutting element coupled to the rotatable shaft, the cutting element having a cup-shaped surface and a cutting edge, the cup-shaped surface being configured to re-direct tissue cut by the cutting edge in a distal direction when the cup-shaped surface moves in the distal direction, wherein the tissue collection chamber has a first closed position capable of retaining cut tissue in the chamber and a second open position capable of allowing expulsion of cut tissue from the chamber, and wherein the tissue collection chamber comprises a displaceable tip at a distal region of the catheter, the displaceable tip having a first closed position capable of retaining cut tissue in the chamber and a second open position capable of allowing expulsion of cut tissue from the chamber, the displaceable tip being attached to the atherectomy catheter in both the first closed and second open positions; placing the catheter in the body lumen; and moving the catheter in the body lumen to contact the cutting element with the material in the body lumen. In one embodiment, the catheter is moved in a distal direction to contact the cutting edge with the material in the body lumen. In an embodiment, the catheter is placed in the body lumen with the cutting element in a stored position and the catheter is moved to contact the material with the cutting element in a cutting position.

In one embodiment, the tissue collection chamber comprises a sheath having a lumen. In one embodiment, the displaceable tip is axially slidable relative to the sheath.

In one embodiment, the method further comprises collecting the material in the tissue collection chamber, removing the catheter from the body lumen, and removing the material from the tissue collection chamber after the catheter has been removed from the body lumen. In an embodiment, the catheter is removed from the body lumen with the tissue collection chamber in the first closed position and the material is removed from the tissue collection chamber with the tissue collection chamber in a second open position capable of allowing expulsion of cut tissue from the chamber.

Referring to FIGS. 1 to 4, an atherectomy catheter 2 is shown which has a cutting element 4 which is used to cut material from a blood flow lumen such as a blood vessel. The cutting element 4 is movable between a stored position (FIG. 2) and a cutting position (FIG. 3) relative to an opening 6 in a body 8 of the catheter 2. The cutting element 4 moves outwardly relative to the opening 6 so that a portion of the element 4 extends outwardly from the body 8 through the opening 6. In one embodiment the cutting element 4 may be positioned relative to the body 8 and opening 6 so that less than 90 degrees of the cutting element 4 is exposed to cut tissue. In other embodiments more of the cutting element 4 may be exposed without departing from numerous aspects of the invention.

Distal end of catheter 2 is positioned near a treatment site in a vessel with cutting element 4 in the stored position. Then catheter 2 is moved distally through the vessel with the cutting element 4 in the working or cutting position as described in further detail below. As the catheter 2 moves through the blood vessel with the cutting element 4 in the working or cutting position the tissue material is cut by the cutting element 4 and is directed into a tissue chamber 12 positioned distal to the cutting element 4. The tissue chamber 12 may be somewhat elongated to accommodate the tissue which has been cut.

In some embodiments catheter 2 has a working length of 30 to 200 cm. In one embodiment catheter 2 has a working length of 135 cm. In some embodiments catheter 2 has a diameter of 4 Fr to 12 Fr (1.3 mm to 4 mm). In one embodiment catheter 2 has a diameter of 7 Fr (2.3 mm).

To expose cutting element 4 through opening 6 cutting element 4 is moved proximally from the stored position so that a cam surface 14 on the cutting element 4 engages a ramp 16 on the body 8 of the catheter 2. The interaction between the cam surface 14 and the ramp 16 causes the cutting element 4 to move to the cutting position and also causes a tip 18 to deflect which tends to move the cutting element 4 toward the tissue to be cut.

The cutting element 4 is coupled to a shaft 20 that extends through a lumen 21 in the catheter 2. Catheter 2 is coupled to exemplary cutter driver 5. Cutter driver 5 is comprised of motor 11, power source 15 (for example one or more batteries), microswitch (not shown), housing 17 (upper half of housing is removed as shown), lever 13 and connection assembly (not shown) for connecting shaft 20 to driver motor 11. Cutter driver 5 can act as a handle for the user to manipulate catheter 2. Lever 13, when actuated to close a microswitch, electrically connects power source 15 to motor 11 thereby causing rotation of cutting element 4. The cutting element 4 is rotated about a longitudinal axis LA when the shaft 20 rotates. The cutting element 4 is rotated at about 1 to 160,000 rpm but may be rotated at any other suitable speed depending upon the particular application. Further description of catheters similar to catheter 2 is found in U.S. patent application Ser. No. 10/027,418 (published as US 2002/0077642 A1) to Patel et al., entitled "Debulking Catheter", the contents of which are incorporated by reference herein.

Figure 5:
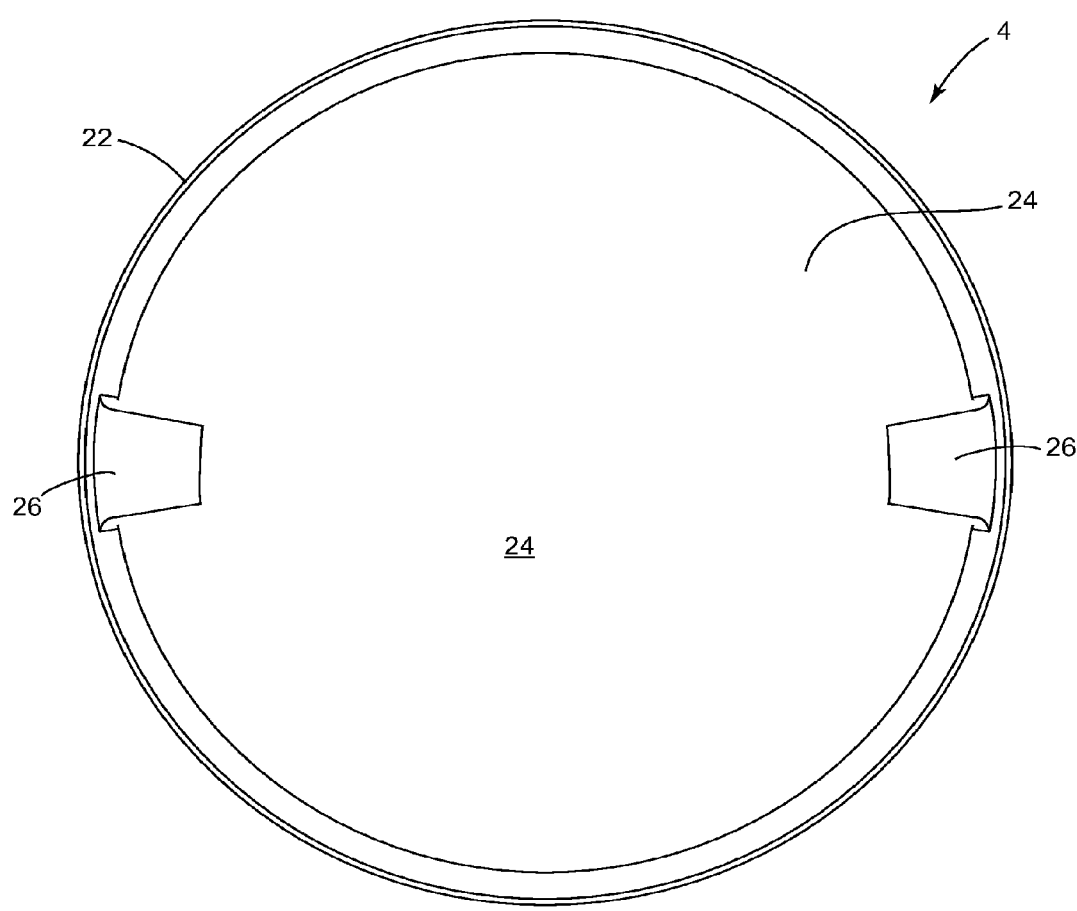
FIG. 5 illustrates an end view of an embodiment of a cutting element.

Referring to FIG. 5, the cutting element 4 is shown when viewed along the longitudinal axis LA. The term "along the longitudinal axis" as used herein shall mean for example the view of FIG. 5 that shows the distal end of the cutting element 4 when viewed in the direction of the longitudinal axis and/or the axis of rotation. The cutting element 4 has a cutting edge 22 that may be a continuous, uninterrupted, circular-shaped edge although it may also include ridges, teeth, serrations or other features without departing from the scope of the invention. The cutting edge 22 may be at a radially outer edge 23 of the cutting element 4 when the cutting element 4 is in the cutting position.

The cutting element 4 has a cup-shaped surface 24, which directs the tissue cut by the cutting edge 22 into the tissue chamber 12. The cup-shaped surface 24 may be a smooth and continuous surface free of throughholes, teeth, fins or other features, which disrupt the smooth nature of the surface 24 for at least half the distance from the longitudinal axis LA to the outer radius at the cutting edge 22. The cup-shaped surface 24 may also be free of any such features throughout an area of at least 300 degrees relative to the longitudinal axis LA. Optionally, one or more raised elements 26 extend outwardly from the cup-shaped surface 24 with FIG. 5 showing two raised elements 26. The raised element 26 is a small wedge of material that rises relatively abruptly from the cup-shaped surface 24. Optionally, some of or all of the cutter may be comprised of an abrasive surface. Further description of additional embodiments usable as cutters in catheter 2 is found in U.S. Patent Application Ser. No. 61/173,845 to Moberg et al., entitled "Methods And Devices For Cutting/Abrading Tissue", the contents of which are incorporated by reference herein.

FIGS. 6, 6A, 7 and 8 illustrate one embodiment of an easily cleaned tissue chamber. Tissue collection chamber 12 is comprised of outer sheath 61 having inward extending edges 61a, one or more slots 61b and distal opening 64 and further comprised of shim sleeve 63 having lumen 68 and window 63w. Shim sleeve 63 is axially slidable relative to outer sheath 61 and inward edges 61a limit the distalmost excursion of shim sleeve 63. Cutter 4 is slidably received within lumen 68 of shim sleeve 63 and can extend through window 63w and window 6. The portion of shim sleeve 63 distal to window 63w is circular in cross section to promote uniform circumferential expansion of distal region 65 when shim sleeve 63 is distally advanced, and is partially circular in cross section proximal to window 6 to allow catheter 2 to bend in the vicinity of ramp 16 (see FIG. 9). Distal region 65 of outer sheath 61 has an expandable diameter due to presence of slots 61b. Distal region 65 forms an expandable tip. In various embodiments 2, 3, 4, 6, 8, 12, 16 or more slots 61b are contemplated. In some embodiments outer sheath 61 is preprogrammed to assume a normally closed position in which distal opening 64 is small or functionally closed such that deposits collected in tissue chamber 12 cannot exit through distal opening 64. With shim sleeve 63 in a first position (FIG. 6) outer sheath distal region 65 has a distally tapering diameter, optionally with distal opening 64. With shim sleeve 63 in a second position (FIGS. 7 and 8) outer sheath distal region 65 has an enlarged diameter, through which cutter 4 can be slidably received. In some embodiments cutter 4 can be extended out of distal opening 64 of outer sheath with shim sleeve 63 in the second position (FIG. 8) due to increased width of slots 61b and enlarged distal diameter of sheath 61. In some embodiments chamber 12 is further comprised of guidewire lumen 66 having proximal opening 66p and distal opening 66d.

Outer sheath 61 may be comprised of thermoplastic polymer, thermoset polymer, thermoplastic elastomer, rubber, nylon, polyimide, polyurethane, or other materials and may further comprise a backbone of resilient material such as for example nitinol or stainless steel. Processes such as extrusion or other processes may be used to fabricate outer sheath 61. Processes such as insert molding, polymer reflow, compression molding, or other processes may be used to fabricate distal end of outer sheath 61. Inward edges 61a can be made by deforming the edges inward, heating the edges in the deformed position and removing the heat to allow the edges to cool and retain the deformed state. Slots 61b can be made by cutting, stamping, laser cutting, may be molded in, or can be made by other processes. Shim sleeve 63 may be comprised of rigid polymer or metal such as polyetheretherketone (PEEK), polyimide, polyester, liquid crystal polymer, nitinol, stainless steel, or other materials, and may be fabricated by processes such as extrusion. Guidewire lumen 66 may be comprised of a tube bonded to outside of sheath 61. In another embodiment sheath 61 may be comprised of bilumen tubing. Guidewire lumen 66 may be comprised of a lumen formed from the wall of outer sheath 61 using thermal processes at least in part.

Figure 2:
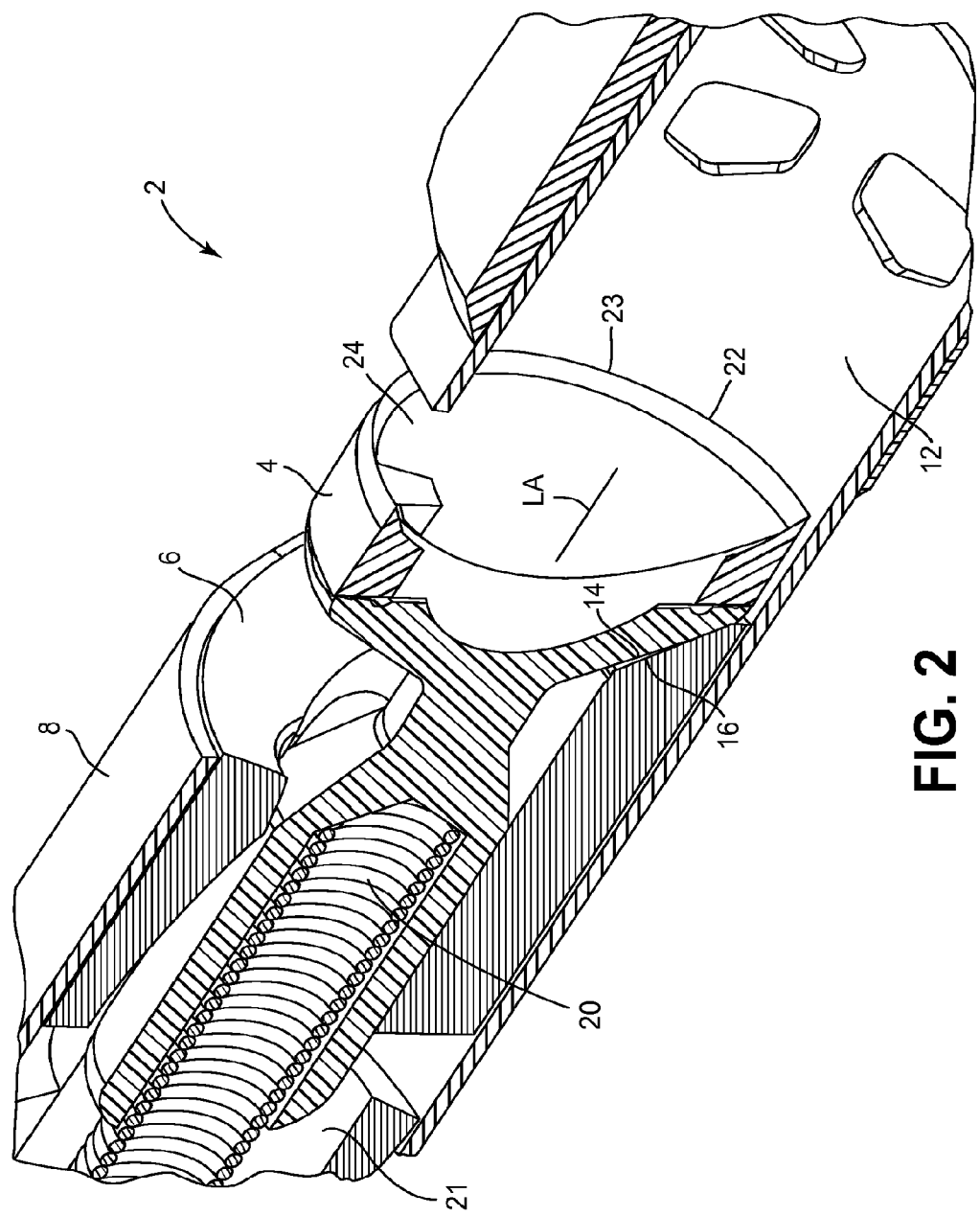
FIG. 2 illustrates an isometric cross-sectional view of a portion of the atherectomy catheter illustrated in FIG. 1 with a cutting element in a stored position.

Exemplary methods of using atherectomy catheter 2 comprised of tissue chamber 12 to cut and remove material from a body of a patient are now described. Using techniques known in the art, a guidewire GW is percutaneously inserted into a patient's body and advanced to a region of interest in a patient's blood vessel V. Using imaging techniques such as fluoroscopy a diseased portion of the vessel is identified and an atherectomy catheter (such as catheter 2) comprised of tissue chamber 12 having appropriate characteristics for treatment site T is chosen. Shim sleeve 63 is positioned such that window opening 63w and window opening 6 are aligned. Catheter 2 is advanced over the guidewire to the treatment site with the cutting element in a stored position (FIG. 2). Using imaging techniques such as fluoroscopy the cutting element is positioned at a desired location relative to (in some methods proximal to) the treatment site.

Figure 3:
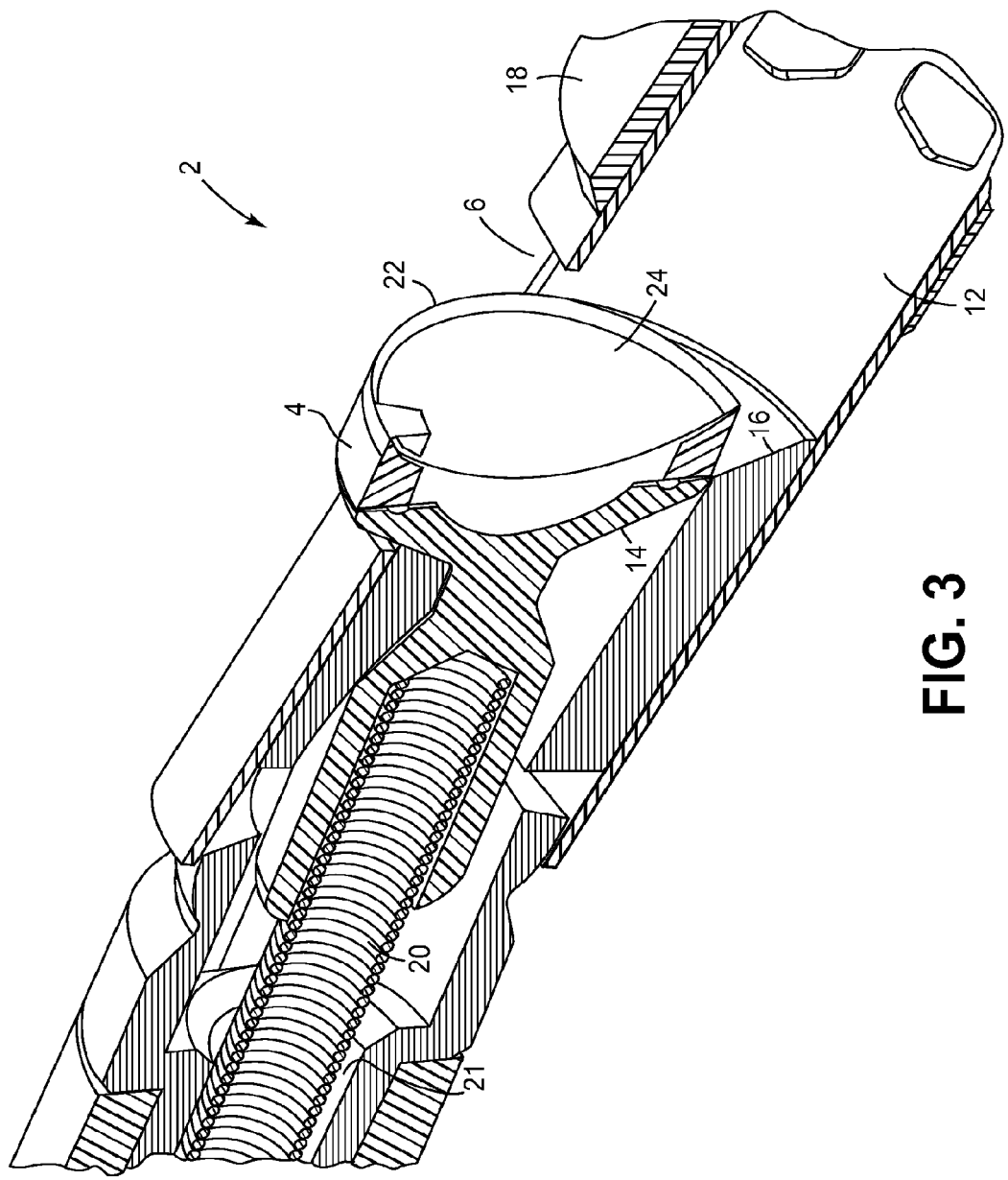
FIG. 3 illustrates an isometric cross-sectional view of a portion of the atherectomy catheter illustrated in FIG. 1 with a cutting element in a working position.
Figure 4:
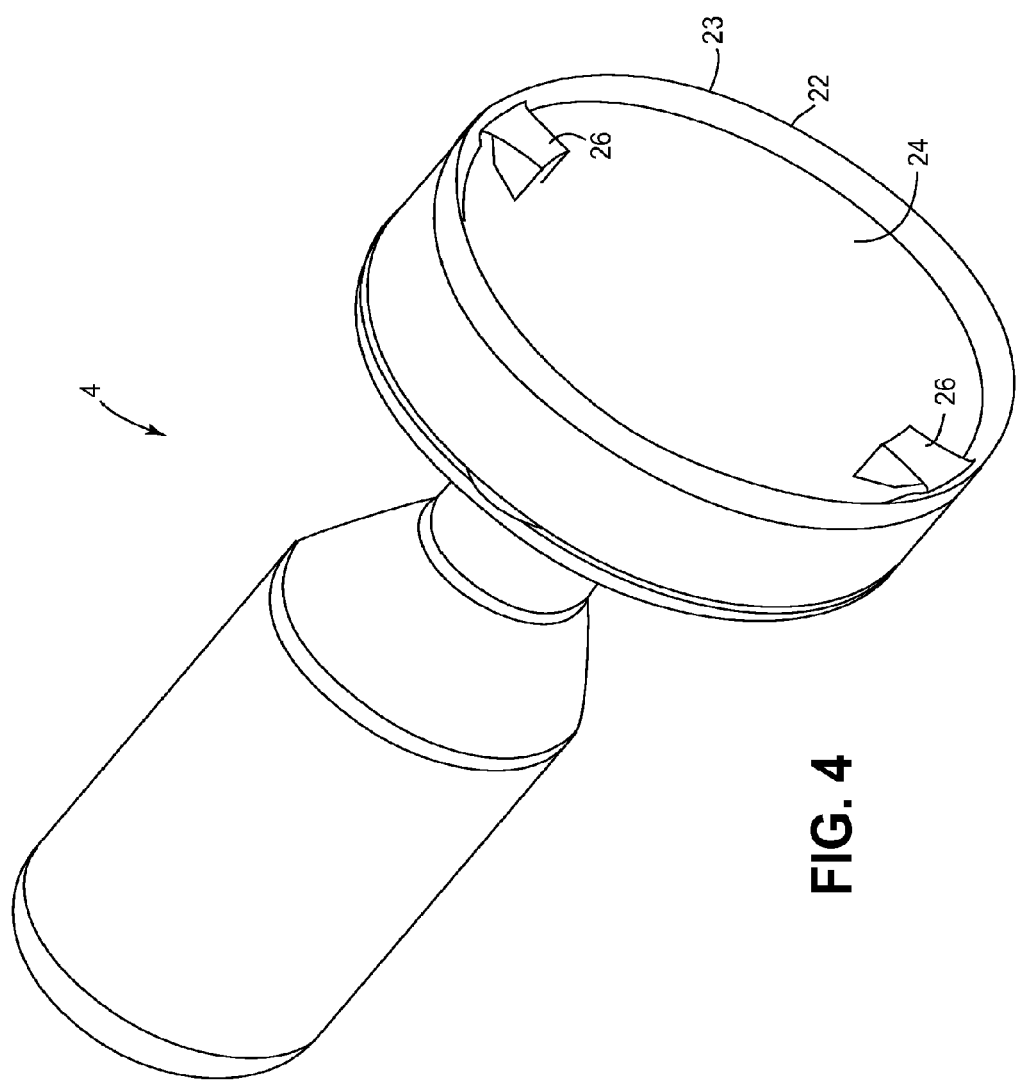
FIG. 4 illustrates an isometric view of an embodiment of a cutting element.

The main body of catheter 2 is held stationary and cutting element 4 is then moved proximally so that the ramp 16 and cam surface 14 engage to move the cutting element 4 to the cutting position of FIG. 3 (i.e. exposed through windows 6 and 63w) and to deflect the tip of the catheter 2 to move the cutting element 4 toward the tissue to be cut. Cutting element rotation about longitudinal axis LA is activated using lever 13. Catheter 2 is advanced distally causing cutter blade 22 to cut material M from luminal surface LS of vessel V. Cup shaped surface 24 directs cut fragments F of material M through windows 6 and 63w into lumen 68 of tissue collection chamber 12 (FIG. 9).

Figure 11:
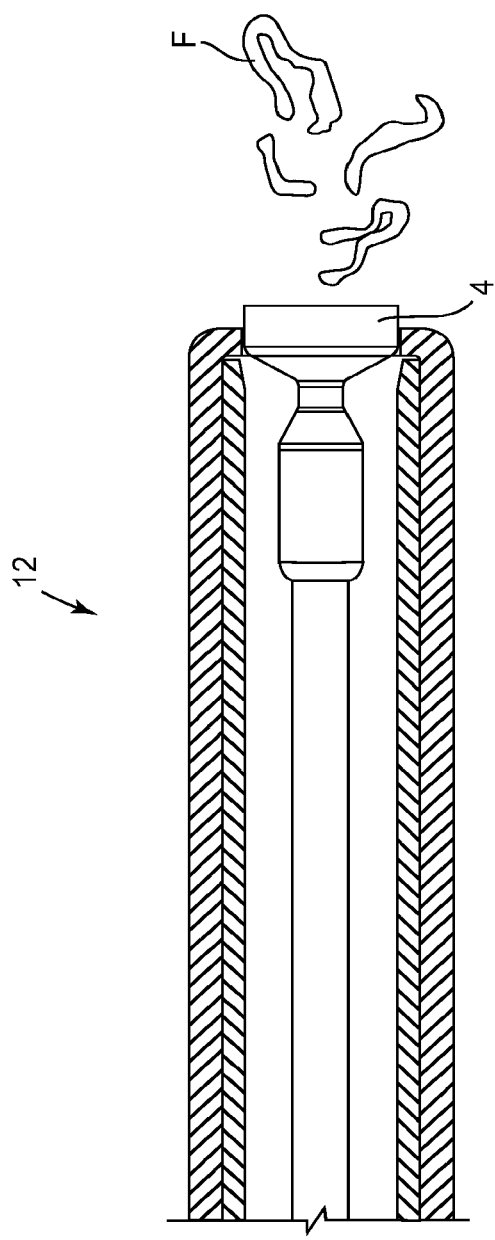

When the catheter operator decides to empty fragments F from tissue collection chamber 12, cutter 4 is advanced distally to move cutter 4 into the stored position and rotation of the cutting element is stopped (FIG. 10). Catheter 2 is retracted proximally and removed from the body. Shim sleeve 63 is next advanced distally to deflect distal portion of sheath 61, causing opening 64 to enlarge and width of slots 61b to widen. In some methods shim sleeve 63 is advanced to contact inward edges 61a of sheath 61. Cutter 4 may then be advanced to expel fragments F from lumen 68 of chamber 12 (FIG. 11) through distal opening 64.

If further material removal from treatment site T is desired, cutting element 4 may be withdrawn to the storage position and shim sleeve 63 can be withdrawn to the first position thereby causing distal region 65 of sheath 61 to return to the closed position. Catheter 2 can then be re-inserted into vessel V and further material may be removed from luminal surface LS as described above.

FIGS. 12 and 13 illustrate another embodiment of an easily cleaned tissue chamber. Tissue collection chamber 12' is comprised of outer sheath 121 having lumen 128 and push shaft 123 attached to tip 125. Push shaft 123 is axially slidable relative to outer sheath 121, is approximately semi-circular in cross section and is received within lumen 128 of sheath 121. Tip 125 has reduced diameter proximal portion 125p which is slidably received within lumen 128 of sheath 121. Cutter 4 is slidably received within lumen 128 of sheath 121 at the same time push shaft 123 is also within lumen 128. Push shaft 123 is rotationally aligned such that window 6 is not blocked by push shaft 123. Distal region 125d of tip 125 may be tapered to a smaller diameter than proximal portion of tip 125p. With push shaft 123 and tip 125 in a first position (FIG. 12) tip proximal portion 125p is slidably received within lumen 128 of sheath 121 and fragments of material removed from the luminal wall of the vessel cannot exit lumen 128 from distal end 121d of sheath 121. With push shaft 123 in a second position (FIG. 13) tip 125 is displaced from distal end 121d of sheath 121 by a distance D and fragments of material removed from the luminal surface of a vessel can exit lumen 128 through distal end 121d of sheath 121. In some embodiments cutter 4 can be extended out of distal end 121d of outer sheath 121 to displace fragments from lumen 128. In some embodiments chamber 12' is further comprised of guidewire lumen 126 having proximal portion 126p and distal portion 126d.

Outer sheath 121 may be comprised of thermoplastic polymer, thermoset polymer, polyimide, polyetheretherketone (PEEK), nylon, or other materials. Processes such as extrusion or other processes may be used to fabricate outer sheath 121. Push shaft 123 may be comprised of rigid polymer or metal such as PEEK, polyimide, polyester, liquid crystal polymer, nitinol, stainless steel, or other materials, and may be fabricated by processes such as extrusion. Tip 125 may be comprised of thermoplastic elastomer, polyether block amide (PEBAX), silicone rubber, or other materials, and may be fabricated by processes such as extrusion, molding, insert molding, dipping, machining, or other processes. Guidewire lumen 126 may be comprised of a tube bonded to outside of sheath 121 and tip 125. In another embodiment sheath 121 may be comprised of bilumen tubing, and in yet another embodiment tip 125 may be comprised of a guidewire lumen therethrough. Guidewire lumen 126 may also be comprised of a lumen formed from wall of outer sheath 121 using thermal processes at least in part.

Exemplary methods of using atherectomy catheter 2 comprised of tissue chamber 12' to cut and remove material from a body of a patient are now described. Using techniques known in the art, a guidewire GW is percutaneously inserted into a patient's body and advanced to a region of interest in a patient's blood vessel V. Using imaging techniques such as fluoroscopy a diseased portion of the vessel is identified and an atherectomy catheter (such as catheter 2) comprised of tissue chamber 12' having appropriate characteristics for treatment site T is chosen. Push shaft 123 is withdrawn to the first position such that distal end 121d of sheath 121 is sealed shut by tip 125. Catheter 2 is advanced over the guidewire to the treatment site with the cutting element in a stored position (FIG. 2). Using imaging techniques such as fluoroscopy the cutting element is positioned at a desired location relative to (in some methods proximal to) the treatment site.

The main body of catheter 2 is held stationary and cutting element 4 is then moved proximally so that the ramp 16 and cam surface 14 engage to move the cutting element 4 to the cutting position of FIG. 3 (i.e. exposed through window 6) and to deflect the tip of the catheter 2 to move the cutting element 4 toward the tissue to be cut. Cutting element rotation about longitudinal axis LA is activated using lever 13. Catheter 2 is advanced distally causing cutter blade 22 to cut material M from luminal surface LS of vessel V. Cup shaped surface 24 directs cut fragments F of material M through window 6 into lumen 128 of collection chamber 12' using methods similar to that illustrated in FIG. 9.

When the catheter operator decides to empty fragments F from collection chamber 12 cutter 4 is advanced distally to move cutter 4 into the stored position and rotation of the cutting element is stopped (FIG. 14). Catheter 2 is retracted proximally and removed from the body. Push shaft 123 is next advanced distally to separate tip 125 from distal end 121d of sheath 121 by distance D, allowing fragments F to exit from distal end of lumen 128. In some methods cutter 4 may be advanced to expel fragments F from lumen 128 of chamber 12' (FIG. 15).

If further material removal from treatment site T is desired, cutting element 4 may be withdrawn to the storage position and push shaft 123 can be withdrawn to the first position thereby causing tip 125 to return to the closed position. Catheter 2 can then be re-inserted into vessel V and further material may be removed from luminal surface LS as described above.

In addition to use in blood vessels the invention is envisioned to be useful for removal of blockages in other lumens such as natural or artificial grafts, stent-grafts, anastomotic sites, fistulae, or other lumens.

The present invention has been described in connection with preferred embodiments but may, of course, be practiced while departing from the above described embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. An atherectomy catheter comprising: a body;
a cutting element coupled to the body and configured for cutting tissue; a tissue collection chamber coupled to the body and comprising:
a sheath having a length, a lumen extending lengthwise, and an expulsion opening in communication with the lumen, at least a portion of the sheath being distal of the cutting element for receiving cut tissue cut by the cutting element; and
a distal tip coupled to the sheath, the distal tip being movable relative to the expulsion opening and lengthwise of the sheath between a closed position, in which the distal tip inhibits cut tissue from exiting the sheath through the expulsion opening, and an open position, in which the distal tip allows expulsion of the cut tissue through the expulsion opening,
wherein the distal tip remains coupled to the sheath in the closed and open positions.

2. The atherectomy catheter set forth in claim 1, wherein the distal tip is movable distally from the closed position to the open position, and is movable proximally from the open position to the closed position.

3. The atherectomy catheter set forth in claim 2, wherein the distal tip has a proximal portion that is slidably received in the lumen of the sheath.

4. The atherectomy catheter set forth in claim 3, wherein the proximal portion of the distal tip has a reduced diameter.

5. The atherectomy catheter set forth in claim 4, wherein the tissue collection chamber further comprises a guidewire lumen, the guidewire lumen having a first portion on the sheath and a second portion on the distal tip.

6. The atherectomy catheter set forth in claim 5, wherein the first and second portions of the guidewire lumen are spaced apart lengthwise of the sheath a first longitudinal distance when the distal tip is in the closed position and a second longitudinal distance when the distal tip is in the open position, wherein the second longitudinal distance is greater than the first longitudinal distance.

7. The atherectomy catheter set forth in claim 1, wherein the distal tip has a proximal portion that is slidably received in the lumen of the sheath for moving the distal tip between the open and closed positions.

8. The atherectomy catheter set forth in claim 7, wherein the proximal portion of the distal tip has a reduced diameter.

9. The atherectomy catheter set forth in claim 1, wherein the tissue collection chamber further comprises a guidewire lumen, the guidewire lumen having a first portion on the sheath and a second portion on the distal tip.

10. The atherectomy catheter set forth in claim 9, wherein the first and second portions of the guidewire lumen are spaced apart lengthwise of the sheath a first distance when the distal tip is in the closed position and a second distance when the distal tip is in the open position, wherein the second distance is greater than the first distance.

11. The atherectomy catheter set forth in claim 1, wherein the expulsion opening extends through a distal end of the sheath.

12. The atherectomy catheter set forth in claim 1, further comprising a rotatable shaft coupled to the body, the rotatable shaft being rotatable about a longitudinal axis of the shaft.

13. The atherectomy catheter set forth in claim 1, wherein the cutting element is movable between a stored position and a cutting position.

14. A method of using the atherectomy catheter set forth in claim 1, the method comprising:
inserting the atherectomy catheter in a body lumen when the distal tip is in the closed position;
cutting tissue in the body lumen using the cutting element so that cut tissue is received in the lumen of the sheath;
withdrawing the atherectomy catheter from the body lumen after said cutting tissue; moving, after said withdrawing the atherectomy catheter, the distal tip from the closed position to the open position; and
removing the cut tissue from the lumen of the sheath through the expulsion opening after said moving the distal tip from the closed position to the open position.

15. The method set forth in claim 14, wherein said moving the distal tip from the closed position to the open position comprises distally moving the distal tip lengthwise of the sheath.

16. The method set forth in claim 15, wherein said moving the distal tip from the closed position to the open position comprises sliding a proximal portion of the distal tip in the lumen of the sheath.

17. The method set forth in claim 14, further comprising:
moving, after said removing the cut tissue from the lumen of the sheath, the distal tip from the open position to the closed position; and
reinserting, after said moving the distal tip from the open position to the closed position, the atherectomy catheter in the body lumen.

18. The method set forth in claim 17, further comprising:
cutting, after said reinserting the atherectomy catheter, tissue in the body lumen using the cutting element so that cut tissue is received in the lumen of the sheath.

19. The method set forth in claim 17, wherein said moving the distal tip from the open position to the closed position comprises sliding a proximal portion of the distal tip in the lumen of the sheath.

20. The method set forth in claim 14, wherein said removing the cut tissue from the lumen of the sheath comprises moving the cutting element distally in the lumen of the sheath to expel cut tissue from the lumen through the expulsion opening.

* * * * *